(12) United States Patent
Tiller et al.

(10) Patent No.: US 8,071,386 B2
(45) Date of Patent: Dec. 6, 2011

(54) METHOD OF MARKING A PRODUCT, MARKED PRODUCT RESULTING THEREOF, AND METHOD OF IDENTIFYING SAME

(75) Inventors: Thomas Tiller, Bussigny (CH); Sylvain Jaquier, Lausanne (CH); Xavier Marguerettaz, Martigny (CH)

(73) Assignee: SICPA Holding SA, Prilly (CH)

( * ) Notice: Subject to any disclaimer, the term of this patent is extended or adjusted under 35 U.S.C. 154(b) by 997 days.

(21) Appl. No.: 10/560,608

(22) PCT Filed: May 19, 2004

(86) PCT No.: PCT/EP2004/005391
§ 371 (c)(1),
(2), (4) Date: Dec. 28, 2005

(87) PCT Pub. No.: WO2005/005933
PCT Pub. Date: Jan. 20, 2005

(65) Prior Publication Data
US 2006/0228802 A1    Oct. 12, 2006

(30) Foreign Application Priority Data
Jul. 2, 2003 (EP) .................................. 03015010

(51) Int. Cl.
*G01N 37/00* (2006.01)
(52) U.S. Cl. ............... 436/56; 436/1; 73/1.24; 149/123
(58) Field of Classification Search ............... 436/1, 56; 149/123; 73/1.24
See application file for complete search history.

(56) References Cited

U.S. PATENT DOCUMENTS

| | | | |
|---|---|---|---|
| 3,894,917 A | 7/1975 | Riseman et al. |
| 5,156,663 A | 10/1992 | Itoh et al. |
| 5,474,937 A | 12/1995 | Anderson, II et al. |
| 5,525,516 A | 6/1996 | Krutak et al. |
| 5,723,338 A | 3/1998 | Rutledge et al. |
| 5,776,713 A | 7/1998 | Garner et al. |
| 5,804,447 A | 9/1998 | Albert et al. |
| 5,843,783 A | 12/1998 | Rutledge et al. |
| 5,849,590 A | 12/1998 | Anderson |

(Continued)

FOREIGN PATENT DOCUMENTS
DE          195 07 301 A      9/1996
(Continued)

OTHER PUBLICATIONS

Response of SICPA Holding S.A. to Written Opinion of the International Preliminary Examining Authority dated Nov. 10, 2005.

(Continued)

*Primary Examiner* — Lyle Alexander
(74) *Attorney, Agent, or Firm* — Greenblum & Bernstein, PLC (57) ABSTRACT

A method and means for identifying the authenticity and the genuine nature of a solid or liquid bulk material, by incorporating a marking composition containing at least one trace ion into the said bulk material, whereby the total concentration of the incorporated trace ions in the market bulk material is chosen to be lower than the corresponding concentration of the same ions in standard sea water. The authenticity and the genuine nature or the adulteration level of the marked bulk material can be tested in-the-field using electrochemical sensors, and confirmed in the laboratory using a method such as atomic absorption spectroscopy, ion chromatography or mass spectrometry.

26 Claims, 2 Drawing Sheets

U.S. PATENT DOCUMENTS

| | | | |
|---|---|---|---|
| 5,942,444 | A | 8/1999 | Rittenburg et al. |
| 5,981,283 | A | 11/1999 | Anderson, II et al. |
| 5,998,211 | A | 12/1999 | Albert et al. |
| 2002/0048822 | A1 | 4/2002 | Rittenburg et al. |
| 2004/0026684 | A1* | 2/2004 | Empedocles .................. 257/14 |

FOREIGN PATENT DOCUMENTS

| | | |
|---|---|---|
| DE | 199 01 041 A | 7/2000 |
| EP | 0327163 B1 | 4/1995 |
| JP | 2002-336798 | 11/2002 |
| WO | 03/058234 A1 | 7/2003 |
| WO | 03/058238 A1 | 7/2003 |

OTHER PUBLICATIONS

Written Opinion of the International Searching Authority dated Oct. 12, 2005.

European Search Report in counterpart European Application No. 03 01 5010, dated Oct. 20, 2003.

Schoeller et al., "Total Body Water Measurement in Humans with 18O and 2H labeled Water", American Journal of Clinical Nutrition, Bethesda, MD, US., vol. 33, No. 12, Dec. 1980, pp. 2686-2693.

Rossman et al., "Multielement Stable Isotope Ration Analysis of Glycerol to Dermineits Origin in Wine", Zeitschrift Fuer Lebensmittel-Untersuchung Und—Forschung. A, European Food Research and Technology, Springer Heidelberg, DE, vol. 207, No. 3, 1998, pp. 237-243.

Nozaki, Encyclopedia of Ocean Science, Vo. 6, pp. 1-11, (Eds.: S.A. Thorpe; J.H. Steele; K.K. Turkian, Academic Press, 2001).

Nozaki, "Rare Earth Elements and their Isotopes in the Ocean", Encyclopedia of Ocean Sciences, vol. 4, pp. 2354-2366, 2001.

Reproduction of Nozaki, "Rare Earth Elements and their Isotopes in the Ocean", Encyclopedia of Ocean Sciences, vol. 4, pp. 2354-2366, 2001.

Office Action issued in counterpart Japanese application No. 2006-517985, dated Dec. 8, 2010, with English Translation.

Written Opinion of the International Preliminary Examining Authority dated Oct. 12, 2005.

Korea Office Action issued in KR 10-2006-7000058, dated Feb. 25, 2011, and English translation.

Office Action issued in counterpart European application No. 04 733 772.0-2204, dated Oct. 29, 2010.

D20 "composition of standard sea water" apparently having a download date of Oct. 22, 2010.

D21 "standard sea water" apparently having a download date of Oct. 22, 2010.

* cited by examiner

METHOD OF MARKING A PRODUCT, MARKED PRODUCT RESULTING THEREOF, AND METHOD OF IDENTIFYING SAME

FIELD OF THE INVENTION

The present invention is directed to the marking of commercial bulk products, so as to allow for the verification of the genuine nature and the absence of dilution of said products. It discloses a method for the invisible in-product marking, as well as corresponding authentication procedures and means which are particularly suitable for field audits. Further, a method for the off-the-field precise laboratory verification of adulteration levels of the said marked bulk products is also given.

BACKGROUND OF THE INVENTION

In a global economy, which facilitates the trans-boundary movement of commercial goods, there is an increasing need, from the side of tax authorities and brand owners, for methods allowing to control the genuine nature of merchandise.

In the particular case of bulk products, such as distilled alcoholic beverages, perfumes, medical preparations, and the like, most counterfeiting is actually performed by replacement or adulteration of the original contents, while recycling original packaging. Bulk products or bulk materials, in general, are divided solid or liquid materials which are handled by volume or by weight.

Material-based security solutions (overt and covert), incorporated into inks and applied through various printing processes, efficiently allow to distinguish genuine packaging from counterfeit one. However, a genuine packaging alone is no warranty by itself for that the product content is genuine too.

Product adulteration, i.e. the 'dilution' of a genuine product with a low-grade counterfeits is hereby of particular concern. For example, a distilled alcoholic beverage, for which the taxes have been paid, might be subsequently diluted to a certain extent with an alcoholic 'back-yard'-product, manufactured out of tax. Such adulteration causes important losses to the state and can also have consequences to public health, in case where the 'back-yard' alcohol of poor quality contains larger amounts of methanol and/or other toxic contaminants.

STATE OF THE ART

The in-product marking and the authentication of bulk products is the object of numerous disclosures of the prior art: U.S. Pat. No. 5,156,653 discloses the marking of petroleum products with latent dyes (added at the level of parts per million), which can be subsequently revealed through a colouring reaction. U.S. Pat. No. 5,980,593 discloses the use of latent fluorescent markers, U.S. Pat. No. 5,498,808 the use of fluorescein esters, all for the same purpose. The use of NIR absorbing or emitting colourless dyes as markers has furthermore been disclosed in U.S. Pat. No. 5,525,516, U.S. Pat. No. 5,998,211, U.S. Pat. No. 5,804,447, U.S. Pat. No. 5,723,338 and U.S. Pat. No. 5,843,783.

The methods and colorants proposed in the cited prior art, although they are suited for the marking of petroleum products, are not appropriate for incorporation into products for human application, such as alcoholic beverages, perfumes and medical preparations, for several reasons:
  i) The products are either not soluble or do not chemically withstand in a largely aqueous environment, such as provided by products for human application;
  ii) the transparent recipients (glass bottles, etc.) in which such products are often commercialised do not sufficiently protect the organic marker from photo-degradation; and
  iii) the addition of markers to a food, drug or perfumery product must be compliant with public health and the prescriptions of regulatory bodies such as the FDA and/or the ATF bureau, which is not the case for most of the cited marking substances of the prior art.

The documents U.S. Pat. No. 5,942,444 and U.S. Pat. No. 5,776,713 disclose biologic marking agents, to be detected with a specific, monoclonal antibody. The technology suffers, however, from certain limitations, too:
  a) The preparation of monoclonal antibodies to specific marker molecules is costly and time-consuming, inhibiting a fast 'change of code' to a new marker and detection system;
  b) the amount of marker which must be present (e.g. 20 ppm in "Eau de Cologne" or in Whiskey) can be observed with the help of modern analytical tools such as GC-MS and HPLC, and this the easier as both methods recommend that no similar chemicals should be present in the product aside the marker, i.e. that there may be no "forest to hide the tree";
  c) the proposed detection system is only of qualitative nature, able to detect the presence of a counterfeit or adulteration, without, however, the capability of quantifying the degree of adulteration.

The document US 20020048822 discloses the marking of a product with a marker molecule which can be electrochemically reduced or oxidised. Presence and amount of the marker is electrochemically determined with the help of amperometric or coulometric electrodes. The proposed preferred authentication method is liquid chromatography (HPLC) separation coupled to an electrochemical detector, which is however not suitable as a field-portable auditing instrument. The method recommends as well that the product should be free of other electroactive compounds, i.e. that there may be no "forest to hide the tree".

The documents U.S. Pat. No. 5,981,283 and U.S. Pat. No. 5,474,937 disclose the marking of liquids by non-radioactive isotopic compounds. The marker is of similar nature as the product to be marked and can thus be perfectly hidden. Only sub-ppm amounts of markers are furthermore required, i.e. typically parts per billion (ppb). The authentication is performed by modern analytical tools, comprising a gas-chromatography (GC) or electro-spray mass-spectroscopy (MS) separation step, followed by a classical fragmentation-mass-spectroscopy (MS) analysis step. However, even this approach suffers from limitations:
  a) The deliberate addition of isotopically marked compounds into food or beverage products is increasingly less tolerated by regulatory authorities;
  b) the cost of isotopic marking compounds is rather high, although the choice of such compounds is almost limitless;
  c) the authentication, by GC-MS or MS-MS, of ppb amounts of markers is time-consuming and requires expensive laboratory equipment and highly skilled operating personnel, which makes it unsuitable for rapid field audits.

It is an object of the present invention to overcome the shortcoming of the prior art, providing for in-product marking methods and means for branded or taxed bulk goods which are suited for human application.

In particular, it is an object of the present invention to provide an invisible marking method and means for identifying the authenticity and the genuine nature of alcoholic beverages, perfumes, and medical preparations, wherein the marking means can be easily incorporated (by mixing or by dissolution) into the said bulk products, are robust against aqueous environment and light, doe not alter the properties (i.e. taste and smell) of the marked products, do not have any negative impact on the health of the consumer, and allow for a qualitative and quantitative determination of the level of adulteration.

It is a further object of the present invention to provide a method of identifying and roughly assessing a correspondingly marked product, which is particularly suited for the screening in the field, and which can be backed by more precise laboratory analyses.

These objects are solved according to the feature of the independent claims.

SUMMARY OF THE INVENTION

The marking method and means for identifying the authenticity and the genuine nature of the present invention applies to bulk materials, that means liquids or divided solids which are handled on a per volume or on a per weight base. The method is particularly suited for bulk materials which are destined to human application, such as food & drink, pharmaceutical preparations or cosmetic products.

The method consists in the incorporation of at least one ion as a marker into the product to be marked. The marker ion or ions for the said applications must be: inexpensive, robust, food grade, naturally occurring in order to not raise regulatory concerns, hidden by naturally occurring similar ions, and declinable in many different keys or combinations of keys.

The product (bulk material) to be marked can be a liquid such as a distilled alcoholic beverage or an Eau de Cologne, or a solid such as a pharmaceutical preparation or a cosmetic product. The marker (or trace) ions are preferably incorporated into the said bulk material by the means of a marking composition containing them in the form of appropriate salts.

The invention is based on the idea that the compounds, especially the ionic compounds which are used for the marking of the product are preferably selected in accordance with a composition of an already naturally occurring material, i.e. sea water. This assures that there are no regulatory concerns about the marking, because sea water is an environment which is compatible with human and animal health for already millions of years. Nevertheless, the addition or incorporation of such compounds and the resulting concentration has to comply with the various and numerous legal requirements in force for food, drugs, cosmetics etc. like for example the laws and regulations concerning drinking water. The amount of marking composition and especially the individual concentrations of the ions incorporated in the marked material or product can be easily kept at non-toxic levels in case the marked material or product is intended for human or animal use.

In the context of the present invention, standard sea water is defined as having the average compositional values listed in Table 1 below. Table 1 refers to sea water samples taken from the North Pacific and having a salinity of 3.5% and is taken from the article of Yoshiyuki Nozaki in the Encyclopedia of Ocean Science, Vol. 6 (Eds.: S. A. Thorpe; J. H. Steele; K. K. Turekian, Academic Press, 2001).

TABLE 1

Estimated mean oceanic concentrations of the elements

| Atomic number | Element | Species | Type of distribution[a] | Oceanic mean concentration (ng kg$^{-1}$) |
|---|---|---|---|---|
| 1 | Hydrogen | $H_2O$ | | |
| 2 | Helium | Dissolved gas | c | 7.6 |
| 3 | Lithium | $Li^+$ | C | $180 \times 10^3$ |
| 4 | Beryllium | $BeOH^+$ | S + n | 0.21 |
| 5 | Boron | $B(OH)_3$ | c | $4.5 \times 10^6$ |
| 6 | Carbon | Inorganic & $CO_2$ | n | $27.0 \times 10^6$ |
| 7 | Nitrogen | Dissolved $N_2$ | c | $8.3 \times 10^6$ |
| | | $NO_3^-$ | n | $0.42 \times 10^6$ |
| 8 | Oxygen | Dissolved $O_2$ | inverse n | $2.8 \times 10^6$ |
| 9 | Fluorine | $F^-$ | c | $1.3 \times 10^6$ |
| 10 | Neon | Dissolved gas | c | 160 |
| 11 | Sodium | $Na^+$ | c | $10.78 \times 10^9$ |
| 12 | Magnesium | $Mg^{2+}$ | c | $1.28 \times 10^9$ |
| 13 | Aluminum | $Al(OH)_3$ | s | 30 |
| 14 | Silicon | $H_4SiO_4$ | n | $2.8 \times 10^6$ |
| 15 | Phosphorus | $NaHPO_4^-$ | n | $62 \times 10^3$ |
| 16 | Sulfur | $SO_4^{2-}$ | c | $898 \times 10^6$ |
| 17 | Chlorine | $Cl^-$ | c | $19.35 \times 10^9$ |
| 18 | Argon | Dissolved gas | c | $0.62 \times 10^6$ |
| 19 | Potassium | $K^+$ | c | $399 \times 10^6$ |
| 20 | Calcium | $Ca^{2+}$ | Almost c | $412 \times 10^6$ |
| 21 | Scandium | $Sc(OH)_3$ | (s#n) | 0.7 |
| 22 | Titanium | $Ti(OH)_4$ | s#n | 6.5 |
| 23 | Vanadium | $NaHVO_4^-$ | Almost c | $2.0 \times 10^3$ |
| 24 | Chromium | $CrO_4^{2-}$ (VI) | | 210 |
| | | $Cr(OH)_3$ (III) | r#s | 2 |
| 25 | Manganese | $Mn^{2+}$ | s | 20 |
| 26 | Iron | $Fe(OH)_3$ | s#n | 30 |
| 27 | Cobalt | $Co(OH)_2$? | s | 1.2 |
| 28 | Nickel | $Ni^{2+}$ | n | 480 |
| 29 | Copper | $CuCO_3$ | s#n | 150 |
| 30 | Zinc | $Zn^{2+}$ | n | 350 |

TABLE 1-continued

Estimated mean oceanic concentrations of the elements

| Atomic number | Element | Species | Type of distribution[a] | Oceanic mean concentration (ng kg$^{-1}$) |
|---|---|---|---|---|
| 31 | Gallium | $Ga(OH)_4^-$ | s#n | 1.2 |
| 32 | Germanium | $H_4GeO_4$ | n | 5.5 |
| 33 | Arsenic | $HAsO_4^{2-}$ (V) | r#n | $1.2 \times 10^3$ |
|  |  | $As(OH)_3$ (III) | r#s | 5.2 |
| 34 | Selenium | $SeO_4^{2-}$ (VI) | r#n | 100 |
|  |  | $SeO_3^{2-}$ (IV) | r#n | 55 |
| 35 | Bromine | $Br^-$ | c | $67 \times 10^6$ |
| 36 | Krypton | Dissolved gas | c | 310 |
| 37 | Rubidium | $Rb^+$ | c | $0.12 \times 10^6$ |
| 38 | Strontium | $Sr^{2+}$ | Almost c | $7.8 \times 10^6$ |
| 39 | Yttrium | $YCO_3^+$ | n | 17 |
| 40 | Zirconium | $Zr(OH)_5^-$ | s#n | 15 |
| 41 | Niobium | $Nb(OH)_6^-$ | ? | <5 |
| 42 | Molybdenum | $MoO_4^{2-}$ | c | $10 \times 10^3$ |
| 43 | Technetium | $TcO_4^-$ | * | * |
| 44 | Ruthenium | $RuO_4^-$ | ? | <0.005 |
| 45 | Rhodium | $Rh(OH)_3$? | n | 0.08 |
| 46 | Palladium | $PdCl_4^{2-}$? | n | 0.06 |
| 47 | Silver | $AgCl_2^-$ | n | 2 |
| 48 | Cadmium | $CdCl_2$ | n | 70 |
| 49 | Indium | $In(OH)_3$ | s | 0.01 |
| 50 | Tin | $SnO(OH)_3^-$ | s | 0.5 |
| 51 | Antimony | $Sb(OH)6^-$ | s? | 200 |
| 52 | Tellurium | $Te(OH)_6$ | r#s | 0.05 0.02 |
|  |  | $TeO(OH)_3^-$ | r#s |  |
| 53 | Iodine | $IO_3^-$ | Almost c | $58 \times 10^3$ |
|  |  | $I^-$ | (r#s) | 4.4 |
| 54 | Xenon | Dissolved gas | c | 66 |
| 55 | Cesium | $Cs^+$ | c | 306 |
| 56 | Barium | $Ba^{2+}$ | n | $15 \times 10^3$ |
| 57 | Lanthanum | $LaCO_3^+$ | n | 5.6 |
| 58 | Cerium | $Ce(OH)_4$ | s | 0.7 |
| 59 | Praseodymium | $PrCO_3^+$ | n | 0.7 |
| 60 | Neodymium | $NdCO_3^+$ | n | 3.3 |
| 61 | Promethium | * | * | * |
| 62 | Samarium | $SmCO_3^+$ | n | 0.57 |
| 63 | Europium | $EuCO_3^+$ | n | 0.17 |
| 64 | Gadolinium | $GdCO_3^+$ | n | 0.9 |
| 65 | Terubium | $TbCO_3^+$ | n | 0.17 |
| 66 | Dysprosium | $DyCO_3^+$ | n | 1.1 |
| 67 | Holmium | $HoCO_3^+$ | n | 0.36 |
| 68 | Erubium | $ErCO_3^+$ | n | 1.2 |
| 69 | Thulium | $TmCO_3^+$ | n | 0.2 |
| 70 | Ytterbium | $YbCO_3^+$ | n | 1.2 |
| 71 | Lutetium | $LuCO_3^+$ | n | 0.23 |
| 72 | Hafnium | $Hf(OH)_5^-$ | s#n | 0.07 |
| 73 | Tantalum | $Ta(OH)_5$ | s#n | 0.03 |
| 74 | Tungsten | $WO_4^{2-}$ | c | 10 |
| 75 | Rhenium | $ReO_4^-$ | c | 7.8 |
| 76 | Osmium | $OsO_4$ | Almost c | 0.009 |
| 77 | Iridium | $Ir(OH)_3$ | s? | 0.00013 |
| 78 | Platinum | $PtCl_4^{2-}$ | c | 0.05 |
| 79 | Gold | $AuOH(H_2O)$ | c | 0.02 |
| 80 | Mercury | $HgCl_4^{2-}$ | (s#n) | 0.14 |
| 81 | Thalium | $Tl^+$ | n | 13 |
| 82 | Lead | $PbCO_3$ | anth.#s | 2.7 |
| 83 | Bismuth | $Bi(OH)_3$ | s | 0.03 |
| 84 | Polonium | $PoO(OH)_3^-$ | s | * |
| 85 | Astatine | * | * | * |
| 86 | Radon | Dissolved gas | c | * |
| 87 | Francium | $Fr^+$ |  |  |
| 88 | Radium | $Ra^{2+}$ | n | 0.00013 |
| 89 | Actinium | $AcCO_3^+$ | n | * |
| 90 | Thorium | $Th(OH)_4$ | s | 0.02 |
| 91 | Protactinium | $PaO_2(OH)$ | s | * |
| 92 | Uranium | $UO_2(CO_3)_2^{2-}$ | c | $3.2 \times 10^3$ |
| 93 | Neptunium | $NpO_2^+$ | * | * |
| 94 | Plutonium | $PuO_2(CO_3)(OH)^-$ | (r#s) | * |
| 95 | Americium | $AmCO_3^+$ | (s#n) | * |

[a]c, conservative; n, nutrient-like, s, scavenged; r, redox sensitive; anth., anthropogenic.

The method of marking a material, preferably a liquid comprises the steps of
- a) identifying at least one ion comprised in the said material at a concentration level of below 50 ppm in the unmarked state;
- b) selecting a marking composition comprising at least one ion as identified in step a), and preferably selecting a said ion from the groups of ions being comprised in standard sea water;
- c) incorporating the marking composition of step b) into the said unmarked material;

wherein the concentration level of the said at least one ion in the marked material is increased in step c) by at least the factor of 3, preferably of 5 and even more preferred of 8 as compared to the concentration level of the ion present in the unmarked material.

The amount of marking composition or ions, respectively which is added to the unmarked material defines an altered concentration level of the at least one ion in the marked product. This concentration level is either measured or calculated and thus defines a reference value of the marking and allows the latter authentication of the marked material or product.

The method for marking and identifying the authenticity of material, preferably an aqueous or non-aqueous liquid, comprises additionally to the already described steps of marking the steps of:
- d) measuring in the marked material the individual concentration of the said at least one ion by the means of a sensor; and
- e) comparing the measured value with at least one reference value and indicating the result of the comparison.

The identification of suitable ions for marking can be based on information which are provided for example by the supplier of the material as a kind of list of ingredients or ionic contents or a laboratory analysis performed by a third party on request of the customer.

The assessment of the specific ions and their concentration in the unmarked bulk product can also be performed by suitable analytical methods, preferably by ion chromatography, atomic absorption, Ion Selective Electrodes or mass spectroscopy. Based on these results the selection of ions or ionic compounds is done afterwards.

A definition of an upper limit for the concentration levels of the ions which are suitable for the use as a marking compound in the marking composition is advantageous since this allows a larger variability of the amount of marking composition added to the unmarked material or product. Further, there are no large risks that someone is violating a law or regulation in case an addition of huge amounts of marking composition is necessary due to an originally high concentration level of the ion used for marking. An upper ion concentration limit of 50 ppm has found to be suitable in general. Depending on the material or product to be marked this upper limit can be shifted to higher values, like 150 ppm or 100 ppm or to lower values, like 20 ppm or 10 ppm. Since the detection limit of electrochemical sensors is around 1 part per billion (ppb; micrograms/kg), the upper concentration limit for an ion suitable for use in a marking composition is high enough to ensure a safe determination of the concentration of an ion in an unaltered material.

Preferably, all those ions which have a concentration around 1 ppb or higher in standard sea water are suited as potential markers in the context of the present invention. Commercially available electrodes are usually capable of determining such low concentrations without the need for a pre-concentration of the samples (which, of course, is also a feasible option in difficult cases, using one of the evaporation- or accumulation/stripping methods known to the skilled in the art).

The marking composition may comprise at least one salt of the group comprising an inorganic or an organic salt. The selected ion may be an inorganic or an organic anion or cation. In case of a liquid product, the marking composition is preferably chosen to be completely soluble in the product.

In particular said ion may be an anion selected from the group comprising fluoride, chloride, bromide, iodide, borate, carbonate, nitrate, phosphate, sulfate, and selenate, or an anion selected from the group of anions comprising the anions of the formula $[M_xO_y(OH)_z]^{n-}$, wherein M is an arbitrary chemical element of the periodic system, and x, y, z, and n are positive integers, and x being greater or equal to 1. Suitable ions are also carboxylic $RCO_2^-$ and sulfonic $RSO_3^-$ acid anions, wherein R is an organic residue or hydrogen.

The ion may also be a cation selected from the group comprising ammonium(+), lithium(+), sodium(+), potassium (+), rubidium(+), cesium(+), magnesium(2+), calcium(2+), strontium(2+), barium(2+), iron (2+/3+), cobalt(2+), nickel (2+), copper(2+), and zinc(2+), or a cation selected from the group comprising the cations of the formula $[M_xO_y(OH)_z]^{n+}$, wherein M is an arbitrary chemical element of the periodic system, and x, y, z, and n are positive integers, and x being greater or equal to 1. Other suitable cations are complex cations, such as ammonium(+) and the organic ammonium derivatives $NR_4^+$ wherein R is an organic residue or hydrogen.

A typical marking composition may include three to four ions in a well defined ratio. By using the ratio of various ions, the number of existing combinations is big enough to offer many marking keys.

The minimal 3-fold excess concentration of the added ion in the marked product in comparison to the concentration in unmarked product or material ensures that the difference is high enough to exceed the value of the standard deviations of measurements methods used. The excess of the ion concentration may preferably be at least five- or better at least eight-fold of the concentration of the ion in the unmarked product or material.

The concentration of the marking composition or the ions comprised in the marking composition, respectively which is added to the unmarked product is determined, either by measurement or by calculation based on the added amount and stored at suitable locations like database, production reports etc. The reference values may also be added directly to the product label as a code which will be readable for authentication purposes.

The marking method according to the present invention are particularly suited for marking bulk products destined to human or animal application or use, in particular products selected from the group of products comprising alcoholic beverages, perfumes, cosmetic products, and pharmaceutical preparations.

A method of identifying the authenticity of a material, especially a material which was marked according to the method described above comprises the steps of:
- a) providing reference values of at least one ion comprised in a marking composition which has been added to the material;
- b) measuring by the means of a sensor an individual concentration of at least one ion in a material to be identified, the sensor being capable of measuring individual concentration values of the ionic compound; and
- c) comparing the measured value with at least one reference value and indicating the result of the comparison.

The reference values are either provided to the authorized personal by the manufacturer of the product who has marked the product or the reference values are already available in form of a code for example applied on the container of the marked material. Beside these ways there are still other ways known to the skilled person to provide reference data.

Said measurement on said marked bulk material is preferably performed in-the-field, as a field-audit, using an electrochemical sensor, preferably an ion-selective electrode, or a multi-ion-selective electrode, or an ion-selective Field Effect Transistor. Such field-auditing allows for a quick checking of liquid merchandise, using a small, hand-held, battery-powered instrument, able to be carried to every place. The used sensor is capable of measuring individual concentration values of the ionic components comprised in the composition, and to give a first in The identification of the authenticity and of the genuine nature of the marked products is preferably performed with the help of electrochemical methods, as known to the skilled in the art. The corresponding equipment is small, field-portable, and able to deliver almost immediately a concentration read-out for a selected ion with the help of a corresponding sensor. Useful sensors comprise ion-selective electrodes, multi-ion-selective electrodes, ion-selective Field-Effect-Transistors, etc. and are commercially available.

The invention relies, as already stated, on the ability to measure the concentration [M] of a marking ion in situ with the help of a selective electrode. Such selective electrodes are known in the art and available from various suppliers for a large number of ions and molecules. During the measurement, the electrode is part of an electrochemical element, comprising a reference electrode (giving a standard potential reference), a working electrode (which is the selective electrode) and an electrolyte (which is the liquid to be analyzed).

The electrochemical element obeys the Nernst Equation, which relates the measured electric potential difference $\Delta E$ to the sought concentration [M] in the electrolyte:

$$\Delta E = \Delta E_{ref} - 0.059 * \log [M]$$

as known to the skilled in the art.

Ion-selective electrodes are widely used for the assessment of aqueous solutions in environmental analysis (both in the field and in the laboratory), in the food & beverage industry, as well as in the biomedical and pharmaceutical industries. Such electrodes are readily available for the anions $F^-$, $Cl^-$, $Br^-$, $I^-$, and the cations $H^+$, $Na^+$, $K^+$. There are also selective electrodes available for certain divalent ions, such as $Ca^{++}$ and $Cu^{++}$.

Because their working principles are known and understood, ion selective electrodes can also be made on purpose for a determined ion. There are basically three types of selective electrodes: a) those based on a glass membrane (for $H^+$, pH electrode); b) those based on an insoluble inorganic salt membrane (e.g. ZnS is selectively sensitive to $Zn^{2+}$ and to $S^{2-}$ ions); and c) those based on ion-exchange or complex-forming resins. Knowing an insoluble salt of, or a selective complex former for a determined ion, it is thus always possible to obtain a selective electrode. The working principle of a selective electrode is very well described and explained in "Electrochemical Methods" (Eds.: A. Bard and L. R. Faulkner, Wiley and Sons, 1980).

Despite of the recommendation for an exclusive use of these ion selective electrodes in aqueous solutions, we surprisingly discovered that the ion-selective electrodes can reliably work in alcoholic beverages containing as much as 50% ethanol, as well as in perfume containing up to 63% ethanol, provided that some care is taken during and after the measurements.

Another suitable electrochemical sensor for determining the authenticity and the genuine nature of marked products in the field according to the invention is the ion-sensitive-field-effect-transistor (ISFET). This type of technology offers the advantage of a sensor manufactured by conventional semiconductor technology, allowing for a high level of integration and miniaturisation of the sensors.

The working principle of an ISFET, described in U.S. Pat. No. 4,816,118 and references therein, is based on a charge build-up on the gate of a MOSFET transistor. To this purpose, the MOSFET transistor, manufactured in a standard CMOS process, has an electrically 'free floating' gate, which is coated with a resin or an inorganic compound, able to selectively interact with the target ions or molecules, adsorbing them to a certain extent. The adsorbed ions from the solution produce an electric field at the gate of the MOSFET, resulting in a change of the current flow through the MOSFET's channel, which is a measure for the target ion or molecule concentrations in the solution. The measurement is taken against a standard reference electrode, as in the case of an ISE. Manufacturers of ISE such as SENTEK Ltd. (UK) offer Combination-ISE sensors, with a reference electrode already included in the sensor. This type of device offers the following advantages for their integration into a portable field audit:

No additional reference electrode needed → compact system
Ideal for unskilled operating persons
No electrode-filling solution needed
Virtually unbreakable
Can be left dry for long periods
Long lifetime
Relatively low cost Combination electrodes can also be obtained from other suppliers, including Metrohm, Analytical Sensors Inc. or Jenway.

For the reasons mentioned, said type of ionic sensor is preferred. However standard ISE sensors can also be used to embody the present invention, provided that a reference electrode is also present.

In addition to the field-auditing step, the method may further comprise an off-the-field laboratory confirmation of a suspect sample which has been collected during the field audit. The off-the-field laboratory analysis is performed by using a high-precision analytical method selected from the group of methods comprising atomic absorption spectroscopy (AAS), ion chromatography (IC), and mass spectrometry (MS) and combinations thereof. All these methods are known to the skilled in the art of analytical chemistry and need not be further described here.

The sensitivity limit of ion chromatography (IC) in aqueous samples for common ions such as fluoride, chloride, nitrite, nitrate, sulfate, lithium, sodium, ammonium, and potassium is in the parts-per-million (ppm) range, using conductivity detectors at the column outlet. On certain types of columns, preconcentration techniques may furthermore be used, i.e. the sample is accumulated at the top of the column under a first set of conditions (generally choice of solvent and temperature), and migrated (separated) under a second set of conditions, pushing the sensitivity to the parts-per-billion (ppb) level. Corresponding equipment is available from Metrohm, Dionex, and others. It is expected that future field-portable ion chromatography equipment will even more enhance the capability of the herein disclosed marking and authentication method.

In a first embodiment of the present invention a distilled alcoholic beverage, having an ethyl alcohol concentration of 20 to 60 Vol % is marked with an marking composition comprising ionic markers. The major constituent of the beverage is water. The preferred marking composition in this case is an inorganic salt or a combination of inorganic salts containing different ions.

Thus, preferred ions are chosen among the group comprising fluorides, chlorides, bromides, iodides, nitrates, sulphates, phosphates, sodium, potassium, magnesium, calcium, and strontium, or a mixture thereof. These ions are occurring naturally in mineral and in sea water. Regarding the amount of added marker, care must be taken to comply with local legislation and not to exceed the maximum admitted level for the said ions in drinking water.

During their manufacturing process, distilled alcoholic beverages are normally diluted, either after the distillation or after the maturing stage. This is done by adding drinkable (spring) water in order to reach the desired percentage of ethyl alcohol (e.g. 40%). It is therefore expected that the final alcoholic beverage product to be marked does already contain some common ions, present in the diluting water. For this reason it is important to analyse the natural ion content of the alcoholic product prior to marking, in order to choose the most appropriate marker ion or combination of marker ions. The natural presence of ions in the to-be-marked product could be seen, at first instance, as a difficulty to implement a marking according to the present invention. However, all to the contrary, it allows, in combination with a carefully chosen marker ion or set of marker ions, to improve the solidity of the marking system, as the already present ions can be taken as forming an integral part of the marking, or as a camouflaging of it.

The ionic marking composition is added in a small proportion, ranging between hundreds of parts per million (ppm) down to 0.1 part per million. The ionic salt(s) can be made up first, but not obligatorily, into an aqueous solution, i.e. a "concentrated" or stock solution which may contain up to 10% solid contents. Said stock solution is subsequently introduced into the liquid to be marked, so as to reach the appropriate concentration levels of ions. The amount of marker(s) present in the alcoholic beverage lies preferably between 50 and 0.01 ppm. More preferably, the amount of marker is between 5 and 0.5 ppm.

The marked product can now be audited by inspectors in the field, to check for the authenticity and genuineness of the product or for its potential adulteration. This is best performed by using portable potentiometric electrochemical Ion-Selective-Electrode (ISE) sensors, which allow for the rapid and selective detection of trace amounts of ions present in an electrolyte.

With respect to the first embodiment of the present invention, the method of marking and/or identifying the authenticity of the bulk material includes following steps:

Determination of the natural ionic content in the alcoholic beverage for the proposed marker.

In-product marking of the alcoholic beverage with at least one ionic compound at the ppm level.

Field inspection to determine the genuine nature of the traded product, or, if the case, its adulteration level using a portable sensor unit, such as an electrochemical sensor, or portable chromatography equipment, such as Ion chromatography.

Off-the-field laboratory inspection to confirm the results on suspect samples and to precisely quantify their adulteration level.

A second embodiment of the present invention is directed to an ionic marking of perfumes. The preferred marking composition in this embodiment is a salt or a combination of salts containing many different ions. As perfumes are products which are not destined to be ingested, the amount and nature of useful ions in the marking is larger than in the first embodiment. Care must be taken however to respect the corresponding legislation.

The ionic marker is added in a small proportion, ranging between hundreds parts per million (ppm) down to 0.1 part per million, preferably between 500 and 0.1 ppm, and even more preferably between 100 and 0.5 ppm. Said addition of marker can be performed using a pre-formed, more concentrated stock solution.

The auditing of the genuine nature of the marked products can be done along the same lines as given for the first embodiment.

In a third embodiment of the present invention the bulk product to be marked are drugs or pharmaceutical ingredients, especially in form of tablets or powders. The preferable marking composition in this embodiment is a salt or a combination of salts containing many different ions. Similar as in the embodiments before a typical marking includes three to four ions in a well defined ratio. By using the ratio of various ions, the number of existing combinations is large enough to create many marking keys.

As pharmaceutical products are destined to be ingested, care must be taken to choose the nature and amount of ions so as to be health compatible and not perturbing or inhibiting the therapeutic effect of the main active ingredient in the drug.

The ionic marking composition is added in a small proportion, ranging between thousand parts per million (ppm) down to 0.1 part per million, preferably between 1000 and 0.1 ppm, and even more preferably between 600 and 1.0 ppm. Said addition of marking composition can be performed by using a pre-formed, appropriately concentrated stock formulation, in which the ionic marking composition is pre-mixed with the pharmaceutical product at a concentration of a few percent. This stock formulation is then added to the final pharmaceutical formulation at the required percentage, either during their manufacturing, or after during the conditioning process. Alternatively, a diluted solution of the marking composition can be dosed to the pharmaceutical product, e.g. the tablets during the packaging (blistering) stage.

Auditing can be performed similar to the way disclosed in the first embodiment. However, because the marked product is a solid, it must be dissolved or dispersed appropriately, before any electrochemical measurements can be made. The various elements composing the field measurement equipment and the various marking and identification steps are similar to the ones described in the embodiments before.

The invention is now described in more detail with the help of examples and figures.

EXEMPLARY EMBODIMENTS

Figure 1:
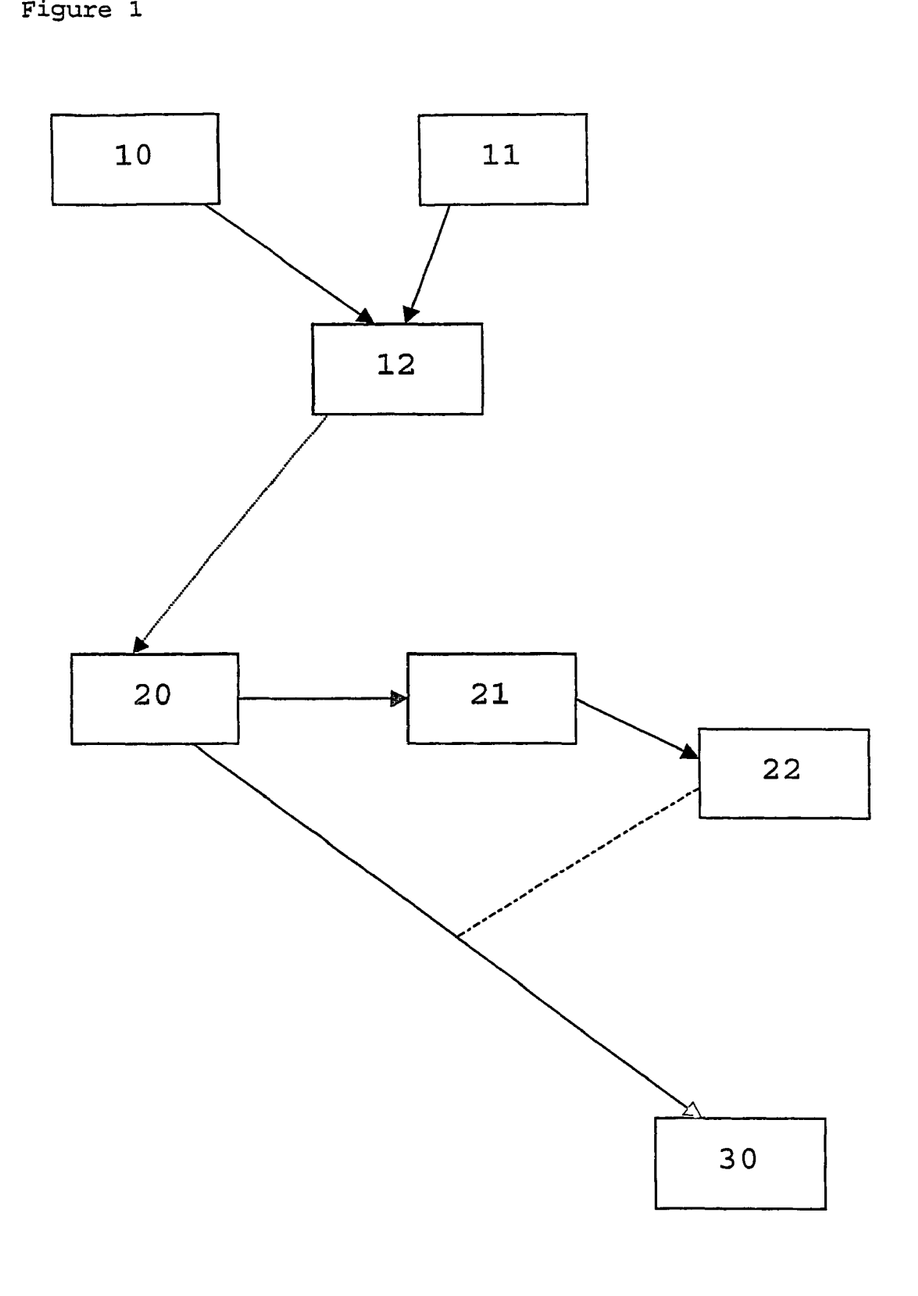
FIG. 1: shows a schematic representation of the marking and identification method.

A schematic overview over the method for marking and determining the authenticity and genuine nature of a bulk product is shown in FIG. 1.

The concentration levels of the ions contained in the product to be marked are determined by suitable methods. From the so obtained list a selection is made of ions which occur in the unmarked product at a concentration level below 50 ppm. Suitable salts of these ions are mixed and thus a pre-fabricated stock solution or powder 10 is prepared.

A pre-fabricated stock solution or powder 10 is blended with the bulk product 11, resulting in a marked bulk product 12. The bulk product 12 is further processed and distributed (not shown).

At a later point in time the distributed batches are tested whether they are still in their genuine condition or if they have been counterfeited or adulterated. A distributed batch 20 is selected and a field audit analysis 21 is done using the appropriate equipment. The result 22 indicates identity, forgery or adulteration of the distributed batch.

If the result 22 indicates any kind of manipulation on the distributed batch 20, a sample is taken for an laboratory analysis 30 in order to confirm the result 22 of the field audit test.

Figure 2:
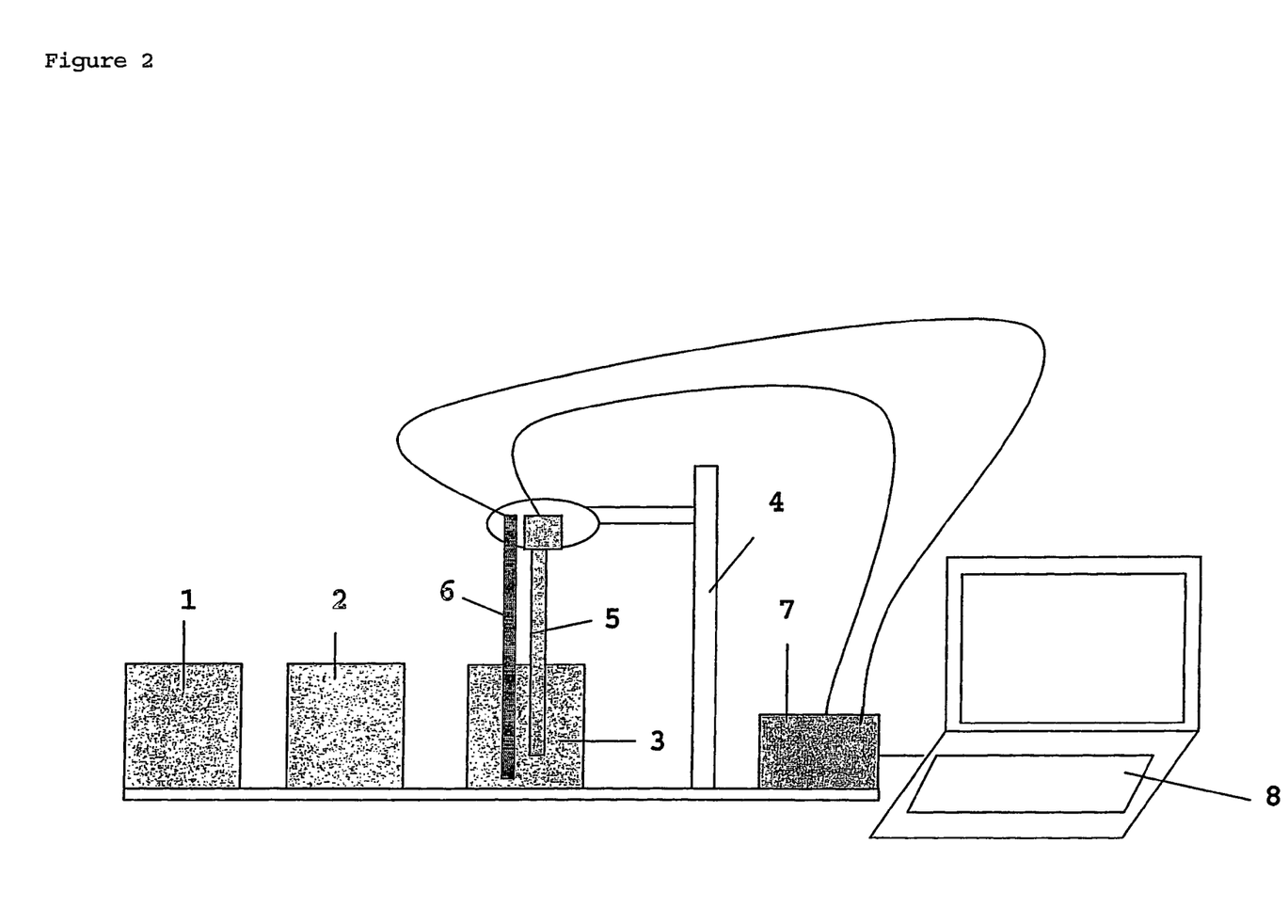
FIG. 2: shows an example of a portable field audit equipment.

The portable field audit equipment according to FIG. 2 comprises the components:
(1) a marked reference solution standard cuvette for calibration;
(2) a de-ionised water cuvette for electrode initial conditioning;
(3) a sample-to-be-audited cuvette;
(4) a stand for the sensor(s);
(5) a combination ISE sensor;
(6) a temperature sensor;
(7) a millivolt-meter with ADC converter; and
(8) a laptop PC with dedicated analysis software.

The marked reference solution 1 is a reference sample of the genuine marked alcohol. It is contained in a 30 ml cuvette and enables for a proper calibration of the sensor. The de-ionized water cuvette 2 contains de-ionized water with ionic marker in a 30 ml cuvette which serves the purpose of conditioning the sensor prior to an initial measurement. The sample cuvette 3 is a 30 ml cuvette containing the sample to be audited. It is preferred that the cuvettes 1, 2 and 3 are identical and that they contain identical volumes of fluid, to increase the precision of the measurement.

The stand for the sensors 4 has the purpose of allowing for identical, reproducible immersion of the sensors in the cuvettes. The electrochemical sensor 5 is a combination ISE electrochemical for instance of the type Fluoride directION, manufactured by SENTEK, Braintree, Essex, UK. Its technical specifications are as follows:

| Ion: | Fluoride ($F^-$) |
|---|---|
| Slope: | −57 mV/decade in concentration |
| Range: | 0.2 to 1900 ppm |

Analog electrodes exist from the same supplier for iodide (Iodide directION), bromide, chloride, sodium(+), potassium (+), calcium(2+), strontium(2+), copper(2+), etc.

The temperature sensor 6, such as a thermocouple, provides information to the analysis software for the compensation of temperature influence in the calculation of the concentration value from the measured electrochemical potential. The millivoltmeter 7, which measures the electrochemical potential, preferably includes an analog-to-digital converter, such as the MeterLess ELITE computer interface, allowing the user to link the Ion Specific Electrode(s) directly to any type of Laptop PC without needing to use a conventional potentiometer or pH-meter. The portable laptop computer 8 contains the appropriate, dedicated analysis software, to calculate the concentration of the marker(s) in the audited product from the measured potential value(s), using the corresponding physico-chemical formulas such as the Nernst law. The result can be presented either in absolute values for the auditor or as a summary displays "Genuine/Counterfeit/Adulteration".

Alternatively, field-portable ion chromatography equipment can also be used for the field-audit in appropriate environments.

EXAMPLE 1

Marking of a Commercial Brandy with Fluoride Ions

The natural ionic content in Fluoride in the brandy to be marked was measured using a Fluoride Ion Selective Electrode and was determined to be below the detection limit (0.2 ppm) of the ISE sensor. Fluoride was consequently determined as being suitable for the marking of the commercial brandy.

A concentrated aqueous stock solution of the marking composition was prepared by dissolving 0.1% w/w of sodium fluoride in high purity distilled water. 0.5 g of the above stock solution was then added to 999.5 g of a commercial brandy to prepare a reference marked brandy having a fluoride concentration of 0.5 ppm.

To simulate criminal adulteration, the reference marked brandy was subsequently "diluted" with non marked brandy to various extend, making up brandies A to E as can be seen in Table 2.

Before starting the authentication measurements, the field detector was activated by dipping the fluoride ISE electrode (SENTEK) for 30 minutes in 1 ppm aqueous sodium fluoride solution. The combination electrode is also connected via the ELIT AD converter to the Laptop computer. This activation is only necessary if the combination electrode is left dried for a few hours. The ISE fluoride detectors was then calibrated by using 20 ml of the reference marked brandy. The voltage output at the combination ISE fluoride electrode was measured via the ELIT interface after dipping the combination electrode for 120 s in the reference sample. This procedure was repeated three times with careful washing with de-ionized water and drying in between. Provided that the three calibration measurements are within 1% difference, the calibration is then validated and the average potential is taken as the calibration value for the marked alcohol.

The marker concentration in the sample A to E was then measured. The combination electrode is immersed in the 20 ml samples and the voltage output taken after 120 s. A careful washing with deionized water and drying of the electrode between the samples is also required. The measured potential value are reported in Table 2 with the corresponding extrapolated and computed concentration level (from Nernst law and calibration measurement). The results obtained are then compared to theoretical values.

From the results it is concluded that sample A is genuine marked alcohol, sample B is counterfeited alcohol and sample C, D, E are genuine marked products which have been adulterated to various extent. The field audit system is precise enough to detect a 10% adulteration level (sample E).

TABLE 2

| Brandy | A | B | C | D | E |
|---|---|---|---|---|---|
| Th. Fluoride concentration (ppm) | 0.5 | 0.0 | 0.2 | 0.3 | 0.45 |
| Measured Voltage (mV) (Field) | 341.25 | 227.29 | 317.82 | 327.66 | 338.34 |
| Cal. concentration (ppm) (Field Audit) | 0.50 | 0.01 | 0.20 | 0.30 | 0.45 |
| Status report (Field Audit) | * | ** | *** | *** | *** |

*: Genuine;
**: Counterfeit;
***: Adulterated

EXAMPLE 2

Marking of a Commercial Whisky with Iodide Ions.

The natural ionic content in Iodide in the whisky to be marked was measured using a Iodide Ion Selective Electrode and was determined to be below the detection limit (0.06 ppm) of the ISE sensor. Iodide was consequently determined as being suitable for the marking of the commercial whisky.

A concentrated aqueous stock solution of the marking composition was prepared by dissolving 0.1% w/w of potassium iodide in high purity distilled water. 1.0 g of that stock solution was then added to 999.0 g of a commercial whisky to prepare a reference marked whisky having an iodide concentration of 1.0 ppm.

To simulate criminal adulteration, the reference marked whisky was subsequently "diluted" with non marked whisky to various extent, making up whiskies A to D as can be seen in Table 3.

Before starting the authentication measurements, the combination iodide ISE electrode (SENTEK Iodide directION) was activated by dipping it for 30 minutes in 10 ppm aqueous potassium iodide solution. The combination electrode is also connected via the ELIT AD converter to the Laptop computer. This activation step is only required if the combination electrode is left dried over a few hours.

The ISE iodide detectors was calibrated by using 20 ml of the reference marked whisky. The voltage output at the combination ISE iodide electrode was measured via the ELIT interface after dipping the combination electrode in the reference sample, stirring it for a few seconds and leaving it at rest for 60 s. This procedure was repeated 5 times with careful quick washing (4 seconds) with de-ionized water and drying in between measurements. Provided that the last three potential measurements are within 2% difference, the calibration is then validated and the average potential of the last three measurement is taken as the calibration value for the marked alcohol.

The marker concentration in the sample A to D was then measured. The measurement procedure was performed as described above for example 1, except that the voltage output was taken after 60 s. Table 3 lists the measured potential values together with the corresponding extrapolated and calculated concentration level (from Nernst law and calibration measurement) and the comparison values with the theoretical values.

TABLE 3

| Whisky | A | B | C | D |
|---|---|---|---|---|
| Iodide concentration (ppm) | 1.0 | 0.0 | 0.5 | 0.9 |
| Measured Voltage (mV; Field) | −126.54 | −35.02 | −94.69 | −121.36 |

TABLE 3-continued

| Whisky | A | B | C | D |
|---|---|---|---|---|
| Extrapolated concentration (ppm) (Field Audit) | 1.02 | 0.03 | 0.30 | 0.83 |
| Status report (Field Audit) | * | ** | *** | *** |

*: Genuine;
**: Counterfeit;
***: Adulterated

From the above field audit results it is concluded that sample A is genuine marked alcohol, sample B is counterfeited alcohol and sample C and D are genuine marked products which have been adulterated to various extent.

EXAMPLE 3

Marking of a Commercial Perfume (Eau de Cologne) with Iodide Ions

The natural ionic content of Iodide in the perfume to be marked was measured using a Iodide Ion Selective Electrode and was determined to be below the detection limit (0.06 ppm) of the ISE sensor. Iodide was consequently determined as being suitable for the marking of the commercial perfume.

A concentrated aqueous stock solution of the marking composition was prepared by dissolving 0.1% w/w of potassium iodide in high purity distilled water. 5.0 g of that stock solution was then added to 995.0 g of a commercial perfume to prepare a reference marked eau de cologne having an iodide concentration of 5 ppm.

To simulate criminal adulteration, the reference marked perfume was subsequently "diluted" with non marked product to various extent, making up perfume A to D as can be seen in Table 4.

Before starting the authentication measurements, the combination iodide ISE electrode (SENTEK) was activated by dipping it for 30 minutes in 10 ppm aqueous potassium iodide solution and connected via the ELIT AD converter to the Laptop computer.

The ISE iodide detector was calibrated according to the calibration procedure as described above for example 2 except that 20 ml of the reference marked eau de cologne were used.

The marker concentration in the sample A to D was then measured. The measurement procedure was identical as describe for example 2. Table 4 lists the measured potential values together with the corresponding extrapolated and calculated concentration level (from Nernst law and calibration measurement) and the comparison values with the theoretical values.

TABLE 4

| Eau de cologne | A | B | C | D |
|---|---|---|---|---|
| Iodide concentration (ppm) | 5.0 | 4.0 | 2.0 | 0.0 |
| Measured Voltage (mV; Field) | 167.09 | −160.25 | −140.69 | −38.63 |
| Extrapolated concentration (ppm) (Field Audit) | 4.97 | 3.81 | 1.77 | 0.03 |
| Status report (Field Audit) | * | *** | *** | ** |

*: Genuine;
**: Counterfeit;
***: Adulterated

From the above Field audit results it is concluded that sample A is genuine marked alcohol, sample D is counterfeited alcohol and sample B and C are genuine marked products which have been adulterated to various extent.

EXAMPLE 4

Marking of a Commercial Drug Tablet (Paracetamol, Acetaminophen) with Iodide and Potassium Ions The natural ionic content of Iodide and potassium in the drug tablet to be marked was measured using a Iodide and a potassium Ion Selective Electrode (by "dissolving" 10% of the drug in water). Both ionic contents were determined to be below the detection limit of the two ISE sensors, namely 0.06 ppm for the Iodide sensor and 0.04 ppm for the potassium sensor. Iodide and potassium were consequently determined as being suitable for the marking of the commercial drug tablet.

A concentrated powder stock product containing the marking composition was prepared by mixing 1% w/w of potassium iodide with commercial drug tablets which have been previously finely crushed with a pillar and mortar. 0.60 g of that stock powder was then added to 9.40 g of a commercial paracetamol tablet to prepare a reference marked paracetamol powder with concentrations of 600 ppm $K^+$ and $I^-$.

To simulate criminal adulteration, the reference marked drug was subsequently adulterated with non marked paracetamol powder product, making up drug A to C as can be seen in Table 5.

Before starting the authentication measurements, the combination iodide and potassium ISE electrodes (SENTEK) were activated by dipping them for 30 minutes in 100 ppm aqueous potassium iodide solution and connected via the ELIT AD converter to the Laptop computer.

The ISE iodide and potassium detectors were then calibrated by using 2.0 g of the reference marked drug powder partially "dissolved" in 18.0 g of deionised water. The further calibration procedure was carried out as described above for example 2 except the use of a solution of the marked drug.

The marker concentration in the sample A to C was then measured. The combination electrode are immersed in a solution made of 2.0 g of paracetamol powder from a crushed tablets and 18.0 g of deionised water. The measurements were performed as described above. Table 5 lists the measured potential values together with the corresponding extrapolated and calculated concentration level (from Nernst law and calibration measurement) and the comparison values with the theoretical values.

TABLE 5

| Drug powder | A | B | C |
| --- | --- | --- | --- |
| Iodide concentration in solution (ppm) | 60.0 | 30.0 | 00.0 |
| Iodide sensor Measured Voltage (mV) (Field) | −234.16 | −213.45 | −69.01 |
| Extrapolated concentration ($I^-$ ppm) (Field Audit) | 59.0 | 26.3 | 0.09 |
| Potassium concentration (ppm) | 60.0 | 30.0 | 0.0 |
| Measured Voltage (mV) (Field) | 78.54 | 50.53 | −38.20 |
| Extrapolated concentration ($K^+$ ppm) (Field Audit) | 60.1 | 20.10 | 0.63 |
| Status report (Field Audit) | G* | A*** | C** |

*: Genuine;
**: Counterfeit;
***: Adulterated

From the above Field audit results it is concluded that sample A is genuine marked drug tablet, sample C is counterfeited drug and sample B is a genuine marked product which has been adulterated to 50% with a non marked product.

The invention claimed is:

1. A method for marking a material, wherein said material is an alcoholic beverage or a perfume, the method comprising:
   identifying at least one non-isotopic ion selected from ions contained in standard seawater in said material present at an initial concentration level of below 50 ppm, said at least one ion being non-toxic with respect to human or animal use; and
   incorporating a marking composition comprising said at least one ion that is non-toxic with respect to human or animal use into the material to form a marked material including said at least one ion in the marked material at an increased concentration by at least a factor of 3 as compared to the initial concentration level.

2. The method according to claim 1, wherein the concentration level of said at least one ion in the marked material is increased by at least a factor of 5, as compared to the initial concentration level of the at least one ion.

3. The method according to claim 1, wherein the concentration level of said at least one ion in the marked material is increased by at least a factor of 8, as compared to the initial concentration level of the at least one ion.

4. The method according to claim 1, wherein said marking composition comprises at least one salt of inorganic salts and organic salts.

5. The method according to claim 1, wherein said at least one ion is at least one inorganic anion.

6. The method according to claim 1, wherein said at least one ion is at least one anion selected from fluoride, chloride, bromide, iodide, borat carbonate, nitrate, phosphate, sulfate, or selenate.

7. The method according to claim 1, wherein said at least one ion is at least one inorganic cation.

8. The method according to claim 1, wherein said at least one ion is at least one cation selected from ammonium(+), lithium(+), sodium(+), potassium(+), rubidium(+), cesium (+), magnesium(2+), calcium(2+), strontium(2+), barium (2+), iron (2+/3+), cobalt(2+), nickel(2+), copper(2+), and zinc(2+).

9. The method according to claim 1, wherein the identifying comprises determining the initial concentration level of said at least one ion.

10. A method for marking and identifying the authenticity of material, wherein said material is an alcoholic beverage or a perfume, the method comprising:
   a) marking a material according to the method of claim 1 to obtain the marked material including an altered concentration level of said at least one ion, the altered concentration level of said at least one ion being defined as at least one reference value;
   b) measuring in said marked material at least one individual concentration of the said at least one ion by means of a sensor; and
   c) comparing said measured at least one individual concentration with the at least one reference value and indicating the result of the comparison.

11. A method according to claim 10, wherein, prior to a), the concentration level of the at least one ion in the unmarked material is determined.

12. The method according to claim 10, wherein said measuring includes determining the at least one individual concentration with an electrochemical sensor in a field audit analysis.

13. The method according to claim 12, wherein said method further comprises an off-the-field laboratory analysis for confirmation of the field audit analysis.

14. The method according to claim 13, wherein said off-the-field laboratory analysis is performed by analytical methods selected from atomic absorption spectroscopy (AAS), ion chromatography (IC), mass spectrometry (MS), or combinations thereof.

15. A method of identifying the authenticity of a material, the material having been marked according to claim 1, the method comprising:

a) providing at least one reference concentration of said at least one ion comprised in said marked material;

b) measuring by a sensor at least one individual concentration of said at least one ion in said marked material, the sensor being capable of measuring individual concentration values of said at least one ion; and c) comparing said measured at least one individual concentration with said at least one reference concentration and indicating the result of the comparison.

16. The method according to claim 15, wherein said sensor is an electrochemical sensor.

17. The method according to claim 15, wherein said sensor is an ion-selective electrode.

18. The method according to claim 17, wherein said ion-selective electrode is a multi-ion-selective electrode.

19. The method according to claim 15, wherein said sensor is a ion-selective field effect transistor.

20. The method according to claim 15, wherein said measuring includes determining the at least one individual concentration with an electrochemical sensor in a field audit analysis.

21. The method according to claim 20, wherein said method further comprises an off-the-field laboratory analysis for confirmation of the field audit analysis.

22. The method according to claim 21, wherein said off-the-field laboratory analysis is performed by analytical methods selected from atomic absorption spectroscopy (AAS), ion chromatography (IC), mass spectrometry (MS), or combinations thereof.

23. A marked material selected from the group consisting of alcoholic beverages and perfumes, obtained according to a method according to claim 1.

24. The method according to claim 1, wherein said at least one ion is at least one anion selected from fluoride, chloride, bromide, iodide, borate, carbonate, nitrate, phosphate, sulfate, or selenate; or at least one cation selected from ammonium(+), lithium(+), sodium(+), potassium(+), rubidium(+), cesium(+), magnesium(2+), calcium(2+), strontium(2+), barium(2+), iron (2+/3+), cobalt(2+), nickel(2+), copper(2+), and zinc(2+).

25. The method according to claim 1, wherein said material is an alcoholic beverage.

26. The method according to claim 1, wherein said material is a perfume.

* * * * *